(12) United States Patent
Heschel et al.

(10) Patent No.: US 6,447,701 B1
(45) Date of Patent: Sep. 10, 2002

(54) METHOD FOR PRODUCING POROUS STRUCTURES

(76) Inventors: Ingo Heschel, Amstelbachstrasse 25, D-52134 Herzogenrath (DE); Günter Rau, Fuchserde 50, D-52066 Aachen (DE)

( * ) Notice: Subject to any disclaimer, the term of this patent is extended or adjusted under 35 U.S.C. 154(b) by 0 days.

(21) Appl. No.: 09/575,863

(22) Filed: May 19, 2000

Related U.S. Application Data (63) Continuation of application No. PCT/DE98/03403, filed on Nov. 18, 1998.

(30) Foreign Application Priority Data

Nov. 19, 1997 (DE) .......................... 197 51 031

(51) Int. Cl.[7] .............................. B29C 67/20
(52) U.S. Cl. ...................... 264/28; 264/49; 264/327
(58) Field of Search .................... 264/28, 327, 49

(56) References Cited

U.S. PATENT DOCUMENTS

| | | | | |
|---|---|---|---|---|
| 2,432,353 A | * | 12/1947 | Talalay | 264/28 |
| 2,610,625 A | | 9/1952 | Sifferd et al. | 128/156 |
| 2,804,653 A | * | 9/1957 | Talalay | 264/28 |
| 3,157,524 A | | 11/1964 | Artandi et al. | 106/122 |
| 3,300,994 A | | 1/1967 | Bagge-Lund et al. | 62/63 |
| 3,424,826 A | * | 1/1969 | Aykanian et al. | 264/28 |
| 3,477,137 A | | 11/1969 | Gelder et al. | 34/5 |
| 3,504,060 A | * | 3/1970 | Gardner | 264/28 |
| 3,784,658 A | * | 1/1974 | Studer | 264/28 |
| 3,812,224 A | * | 5/1974 | Smith et al. | 264/28 |
| 3,864,840 A | | 2/1975 | Baskin | 34/5 |
| 4,412,947 A | * | 11/1983 | Cioca | 264/49 |
| 4,501,719 A | | 2/1985 | Williams | 422/102 |
| 4,522,753 A | * | 6/1985 | Yannas et al. | 264/28 |
| 4,531,373 A | | 7/1985 | Rubinsky | 62/63 |
| 4,590,684 A | | 5/1986 | Arsem | 34/5 |
| 4,687,672 A | | 8/1987 | Vitkovsky | 426/524 |

FOREIGN PATENT DOCUMENTS

| | | |
|---|---|---|
| DE | 656555 | 11/1959 |
| DE | 1 803 420 | 10/1968 |
| DE | 26 25 289 | 6/1976 |
| DE | 27 37 745 | 8/1977 |
| DE | 38 17 906 A 1 | 5/1988 |
| DE | 38 32 162 A 1 | 9/1988 |
| DE | 40 28 622 A 1 | 9/1992 |
| DE | 43 28 329 A 1 | 8/1993 |
| DE | 44 14 757 A 1 | 4/1994 |
| DE | 44 15 844 A 1 | 5/1994 |
| DE | 297 14 492 U 1 | 8/1997 |
| EP | 0 069 176 | 1/1983 |
| EP | 0 317 411 | 11/1988 |
| EP | 0 747 068 | * 12/1996 |
| JP | 58074103 | 4/1983 |
| JP | 61-191609 | 2/1985 |
| WO | WO89/12407 | 12/1989 |

OTHER PUBLICATIONS

Dr. J.A. Wieringa et al., "Droplet Breakup in the Emulsification of non–Newtonian Fluids", 1994, Chem. —Ing.-Tech. 66, Nr.9, S. 1165–1276.

(List continued on next page.)

*Primary Examiner*—Allan R. Kuhns
(74) *Attorney, Agent, or Firm*—Steven J. Hultquist; Marianne Fuierer; Yongzhi Yang

(57) ABSTRACT

A method for producing porous structures in which a liquid or pasty mixture of substances is brought at least partially to solidification and subsequently freeze-dried.

20 Claims, 3 Drawing Sheets

OTHER PUBLICATIONS

Dr. med. A. Sputtek et al., "Tieftemperaturkonservierung menschlicher roter Blutkörperchen mit dem Kryprotekiv Hydroxyethylstärke (HES)—Bedeutung der Abkühlrate", 1994, Chem. –Ing—Tech. 66, Nr. 9, S. 1165–1276.

Dipl.–Phys Th. Groβ et al., "Verfahren zur Kryokonservierung isolierter Herzmuskelzellen für die kardiophysiologische and pharmakologische Forschung", 1994, Chem. –Ing—Tech.66, Nr. 9, S. 1165–1276.

Dipl.–Ing. G. Spieles et al., "Sekundäre Trocknung and Glasübergang bei der Gefriertrocknung biologischer Materialien", 1994, Chem –Ing—Tech. 66, Nr. 9, S. 1165–1276.

Kerstin Pralle et al., "Gefriertrocknung von Mikroorganismen: II. Enfluβ des Einfriervorgangs auf die überlebenstrate*", 1991, Chem.–Ing.–Tech. 63, Nr. 5, S. 510–511.

Hans–Hermann et al., "Gefriertrocknung von Mikrooganismen 1.Experimentelle Methoden und typische Ergebnisse*", 1990, Chem.–Ing.–Tech. 62, Nr. 2, S. 148–149.

* cited by examiner

METHOD FOR PRODUCING POROUS STRUCTURES

This application is a continuation under 35 U.S.C. 120 of International Patent Application No. PCT/DE98/03403, filed Nov. 18, 1998.

1. FIELD OF THE INVENTION

The invention relates to a method for producing porous structures in which a liquid or pasty mixture of substances is brought at least partially to solidification and subsequently freeze-dried.

2. BACKGROUND OF THE INVENTION

Sponges for cosmetic and medical applications can be manufactured by freezing an aqueous basic suspension by lowering its temperature and subsequently freeze-drying the frozen material. This method typically involves filling the basic suspension into metal bowls, which are subsequently cooled down from underneath using a cold brine, so that the basic suspension solidifies. This involves the suspension first solidifying at the bottom of the bowl and then also in the entire bowl. As a consequence of the expansion of the ice, a solidifying structure is provided, that after the process produces a very irregularly porous sponge with variously distributed density and various different pore orientations.

Another known method involves freeze-drying products in small bottles. This method involves the generation of a very varied solidifying structure in radial directions inside the small bottle. Supercooling in the outer areas of the bottle leads to the formation of globule-like ice crystals, while the solidification process is dendritic or cellular in the inner area of the bottle.

These differentiated degrees of porosity inside the product obstruct freeze-drying, as less porous areas of the structure generate strong material transport resistances. Moreover, products with homogeneous porosity are of great importance for many technical and medical applications.

3. SUMMARY OF THE INVENTION

It is an object of the invention to provide a process for producing products with a more homogeneous structure than the above-described processes.

In one aspect, the invention relates to a method for producing porous structures, in which a liquid or pasty mixture of substances is brought at least partially to solidification and subsequently freeze-dried The mixture is preferably cooled down between two surfaces with different temperatures that can be tempered and are set at a distance from each other which results in the generation of a substantially ordered or homogeneous structure during the solidification process.

In one aspect of the invention, the difference between the temperatures of the opposing surface areas is kept substantially constant during the cooling process. In another aspect, the temperature of one surface area is kept constant until the other surface area has cooled down sufficiently for the desired gradient to be created. The surfaces may be arrayed parallel to each other or are arrayed concentrically.

In another aspect of the invention, the mixture is introduced on a first side between the surfaces and on a second side is let out between the surfaces, while the temperature of the opposing surface areas drops from the first side to the second side. The mixture may, in a particular aspect of the invention, be fed through or along heat-conducting conveyor belts or hoses.

In a preferred aspect of the invention, the at least partially solidified product is freeze-dried, as one surface is removed and the other surface is tempered.

The liquid or pasty mixture may comprise or may consist of an aqueous solution or suspension. The liquid or pasty mixture may comprise an active ingredient, e.g., a biologically active material, living cells and/or a cryoprotective substance. Such materials (e.g., active ingredient, biologically active material, living cells and/or cryoprotective substance) may be added directly to the liquid or pasty mixture and may additionally (or alternatively) be added directly to the freeze-dried structure.

In another aspect, the invention relates to a method for producing porous structures in which a liquid or pasty mixture of substances is brought at least partially to solidification and subsequently freeze-dried, wherein the mixture is pre-cooled under pressure and subsequently suddenly depressurized. In a preferred embodiment, the pressure is in the range from 1 to 250 MPa. Additional gases may also be dissolved in the mixture.

In a related aspect, after cooling has been completed, the mixture is warmed back up to and temporarily maintained at a re-crystallization temperature before being freeze-dried.

In another aspect, foreign materials in preferred geometries and orientations are introduced into the liquid or pasty mixture and removed after the freeze-drying.

The methods of the invention are suitably employed in the manufacture of medicinal or pharmaceutical products or products of environmental and biotechnology, and are also suitable for producing sponges for cosmetic or medicinal purposes.

5. DETAILED DESCRIPTION OF THE INVENTION

In one aspect, the invention provides a process in which the mixture is cooled down between two surfaces with different temperatures that can be tempered and are set at a certain distance from each other, preferably in such a way that an ordered structure is generated during the solidification process.

This temperature control causes a crystalline structure to grow from the cooler surface towards the warmer one. Meanwhile, the front of crystals grows continuously from the one surface to the other, resulting in a substantially homogeneous distribution between crystalline and non-crystalline structures to be generated in the specimen. The subsequent freeze-drying is facilitated by the homogeneous crystalline structure and leaves the substantially homogeneously porous structure free by evaporating or sublimating the crystalline and liquid components. The resulting structure can be influenced optimally by adjusting the temperature gradient or the speed at which the solidification front advances.

The difference between the temperatures of the opposing surface areas is advantageously kept substantially constant during the cooling process. A constant temperature difference results in a practically constant speed of the advance of the ice front between the surfaces and thus leads to a particularly homogeneously porous structure.

In the case of biological specimen materials, it is often impossible to raise the temperature any higher than 37 to 40° C., as this would lead to the generation of cell damage or denaturation. In such cases, the temperature of one surface area is preferably maintained at a maximally permissible, harmless temperature long enough for the opposing surface area to have cooled down sufficiently for the desired gradient to be created. This process permits the formation of a substantially homogeneous sponge structure with minimal or no damage to cells or proteins.

One simple method for executing the process of the invention provides for the surfaces to be arrayed parallel to each other. The mixture is fed between these surfaces in their parallel array and cooled down in such a way that the crystal formation advances from one surface to the other one.

The warmer surface delimitation of the mixture may be tempered directly by heat radiation or convection.

Depending upon the porous structure needed, the surfaces may also be arrayed concentrically. Either the inner or the outer surface can be kept warmer, so that the crystal formation advances either from the inside outwards or from the outside inwards.

Depending on how the surfaces are arrayed, the method of the invention produces crystalline structures running radially or in parallel that can stretch across the entire area between the surfaces or just fill part of the area.

One particularly advantageous embodiment of the invention provides for the mixture to be introduced on a first side between the surfaces and on a second side let out between surfaces, while the temperature of the opposing surface areas drops from the first side to the second side. This enables a liquid or a pasty mixture to be solidified continuously, whether the surfaces are arrayed parallel to each other or concentrically. Ideally, the liquid or pasty mixture is introduced at one point of the device and the porous structure is removed continuously from the other extremity of the device.

In the case of continuous processes, it is advantageous for the mixture to be fed through or along heat conducting conveyor belts or hoses. Conveyor belts or hoses conducted to the opposing surfaces enable the mixture to be transported continuously or discontinuously in relation to the surfaces and obstruct any direct contact between the surfaces and the mixture. In this case, the specimen may be moved relative to the belts or hoses or fed past the surfaces together with the belts or hoses.

One particularly simple method of freeze-drying is made possible if the at least partially solidified product is freeze-dried with one surface being removed and the other surface being tempered. After the one surface has been removed, the at least partially solidified product is freely accessible for an applied negative pressure, which removes the ice phase and other unfrozen water from the upgraded phase by processes of sublimation, desorption and diffusion.

The surface that is already tempered when the temperature gradient is adjusted during the solidification process is also tempered during the freeze-drying, in order to control the freeze-drying process.

The invention provides above all for an aqueous suspension being used as the liquid or pasty mixture. The aqueous phase is easy to remove by freeze-drying and enables porous structures such as sponges to be produced that can be used in many ways, especially in medical technology.

If no additives are added to the liquid or pasty mixture to influence the crystalline structure, the process can be ordered in such a way that the crystal growth does not result in displacing or changing the orientation of the foreign phase particles such as fibers. In this way, the method of the invention can be used to generate very ordered structures, with a very homogeneous distribution of foreign phase particles that substantially replicates the distribution in the liquid or pasty mixture. After freeze-drying, the result is therefore one of very fine structures that may be advantageous for example as sponges for absorbing liquids, e.g. for staunching blood or treating burn wounds, but also as bio-material for generating tissue, such as cartilage.

For other applications, it is particularly advantageous if the liquid or pasty mixture is enriched with active ingredients or additives. Thus salts or acids can be added, for example, for the purpose of influencing the crystalline structure of the liquid mixture. In The method of the invention, ice crystals shaped for example like fingers or like little trees (dendritic crystals), which are capable of changing the orientation of the suspended foreign phase particles, will then grow through the liquid or pasty mixture. During the subsequent freeze-drying, these finger-shaped ice crystals sublimate, leaving homogeneously open pores. The ice crystal structure and thus the subsequent pore structure can be influenced both by the way that the process is applied during cooling (the temperature gradient over the specimen and the speed of advance of the ice front) and by the type and concentration of the additives used.

Further additives can be added for the purpose of influencing the solidity properties of the structures generated. In the case of a collagen suspension, for example, harder structures can be generated by adding hydroxy apatite, making the sponge more suitable for use as a bone substitute material. Moreover, it is advantageous in medical implants, for example, to enrich the liquid mixture with biologically active substances or even living cells with antifreeze additives that contribute to improving the desired biological processes when the porous structures are applied. Antibiotics can be added, for example, in order to target defense against infection. In order to accelerate the healing of wounds, for example by colonizing the structures with cells or causing vessels or nerves to grow into them, peptides, proteins or enzymes can be added as biologically active substances that encourage cellular adhesion or cellular growth in the structures, for example. Biological cells, such as chondrocytes, fibroblasts, keratinocytes and endothelial cells, encourage the formation of a new cellular matrix or of a monolayer of cells or a vessel and produce important substances that contribute to healing wounds. Hydroxyethyl starch as an example of a macromolecular cryoprotection—possibly enriched by adding certain sugars—restricts cellular damage during the freezing process and is also suitable for freeze-drying. After being rehydrated with body liquids or solutions, sponges generated in this way can carry out special biological or medical functions.

The active ingredients or additives, biologically active materials or living cells mentioned above can also be added to the generated structure after freeze-drying, as the porous construction facilitates the disposition of these substances in the structure.

One particularly advantageous application of the method of the invention consists of using it for medicinal or pharmaceutical products or products of environmental and biotechnology. In these fields, sponges for cosmetic or medicinal purposes are especially significant, particularly in the field of tissue engineering.

The invention also provides a method for manufacturing porous structures in which a liquid or pasty mixture of substances is caused (at least partially) to solidify and is subsequently freeze-dried, while the mixture is pre-cooled under pressure and subsequently suddenly depressurized.

This aspect of the invention involves preferably cooling the mixture under pressure until shortly before the point of solidification, while the sudden depressurization leads to a crystallization of the cooled liquid mixture, wherein there is a simultaneous formation throughout the entire mixture of homogeneously distributed ice crystals that, according to the temperature and the pressure control, continue to grow or remain small and are spread out by the freeze-drying, so that a substantially homogeneously porous structure results. The temperature and pressure control enable either a large number of smaller crystals or a smaller number of larger crystals to be generated, so that fine pore or large pore structures result. It is advantageous if the pressure in the area is in the range from 1 to 250 MPa.

If additional gases are dissolved in the liquid mixture, the crystallization can be exploited to generate greater porosity and lower density in the structure, by means of gas pocket nucleation. This possibility of generating greater porosity is suitably employed in the aspect of the invention using pressure reduction and in the above-described variant without pressure reduction.

One further advantageous variant for generating greater porosity consists of intervening after the solidification of the specimen according to the invention, in order to undertake its re-crystallization in the vicinity of the solidification temperature and to follow up with the freeze-drying phase only after this. This method is useful for causing smaller crystalline areas to grow together to form larger accumulations, which generates larger pores.

Furthermore, all the variants can make use of the possibility of introducing foreign materials in preferred geometries, such as fibers, in the liquid or pasty mixture, which can be removed from the specimen after the freeze-drying, so that the porous structure is additionally determined by the geometry and location of these foreign materials.

One example of an embodiment of the method of the invention is illustrated in the drawings and is explained in greater detail hereunder.

Figure 1:
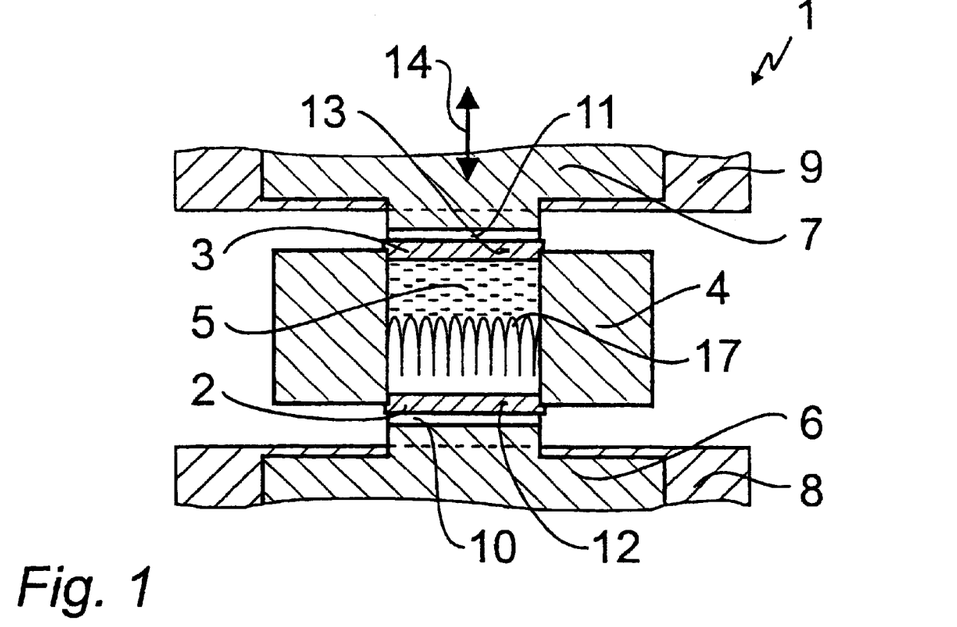
FIG. 1. A device for producing porous structures in the batch process.

The device 1 illustrated in FIG. 1 has a lower specimen delimitation 2 and an upper specimen delimitation 3, between which the specimen space is arrayed within an insulating specimen framework 4. The lower and the upper specimen delimitations 2 and 3 are identical in construction and have the purpose of tempering the specimen arrayed between these said specimen delimitations in the specimen space 5 during the solidification process and in case of need also during the freeze-drying process. The tempering is achieved by means of copper blocks 6 and 7, which are embedded laterally in a heat insulation mantel 8 and 9. An electrically powered membrane heating element 10 or 11 whose purpose is compensation heating is situated in each case between the copper blocks 6 and 7 and their respective lower and the upper specimen delimitations 2 and 3. The specimen delimitations 2 and 3 are equipped with temperature measurement points 12 and 13, so that an exact temperature control can be executed by means of the cooled copper blocks 6 and 7 and of the membrane heating elements 10 and 11.

In order to introduce the specimen into and remove it from the specimen space 5, the upper specimen delimitation 3 can be lifted pneumatically or hydraulically by means of a spindle 14, whose presence is indicated schematically in the drawing as a double-headed arrow.

The device can be installed in a closed vacuum chamber with a condenser (not illustrated), so that, if the need arises, the freeze-drying process can be carried out in direct sequence. The process of freeze-drying calls for the vacuum chamber to be emptied of air, while the lower membrane heating element 10, for example, may be used to temper the specimen during the freeze-drying.

Figure 2:
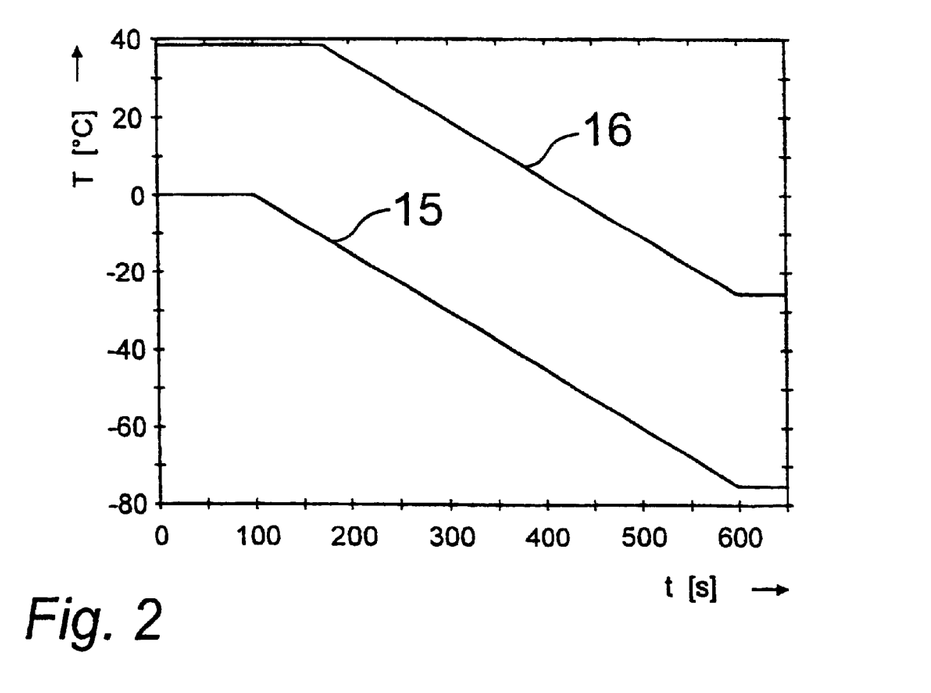
FIG. 2. An example of temperature control at various points of the specimen over the course of time.

In FIG. 2, the temperature gradients over the course of time are reproduced schematically. The lower curve 15 shows the temperature gradient on the lower specimen delimitation 2, while the upper curve 16 shows the temperature gradient on the upper specimen delimitation 3. As the specimen delimitations are arrayed at a distance of 10 mm from each other, the lower curve 15 is also described as "x=0 mm" and the upper curve 16 as "x=10 mm".

By means of the copper blocks 6 and 7 and the heating elements 10 and 11, depending on the time, the specimen delimitations 2 and 3 are kept precisely to the temperatures illustrated in the diagram. In the case illustrated, this involves the growth of the ice front 17 with a cellular structure from the lower to the upper specimen delimitation. To this end, the temperature is adjusted in such a way that the difference between the temperature at the lower specimen delimitation 2 and the temperature at the upper specimen delimitation 3 is kept constant. As, however, in the interests of avoiding damage to the cells, a given maximum temperature may not be exceeded, the temperature difference is kept slightly smaller during the first phase of the cooling process. This enables a regulated temperature reduction with a constant rate of cooling to be set. The aim is for the ice front to advance through the specimen at a practically constant speed, so that very regular ice structures are generated throughout the entire specimen, whose geometries can be influenced, among other things by the choice of the temperature gradients between the lower and the upper delimitation surfaces and by the rate of cooling at which the temperatures of the two delimitations are reduced.

Figures 3, 4:
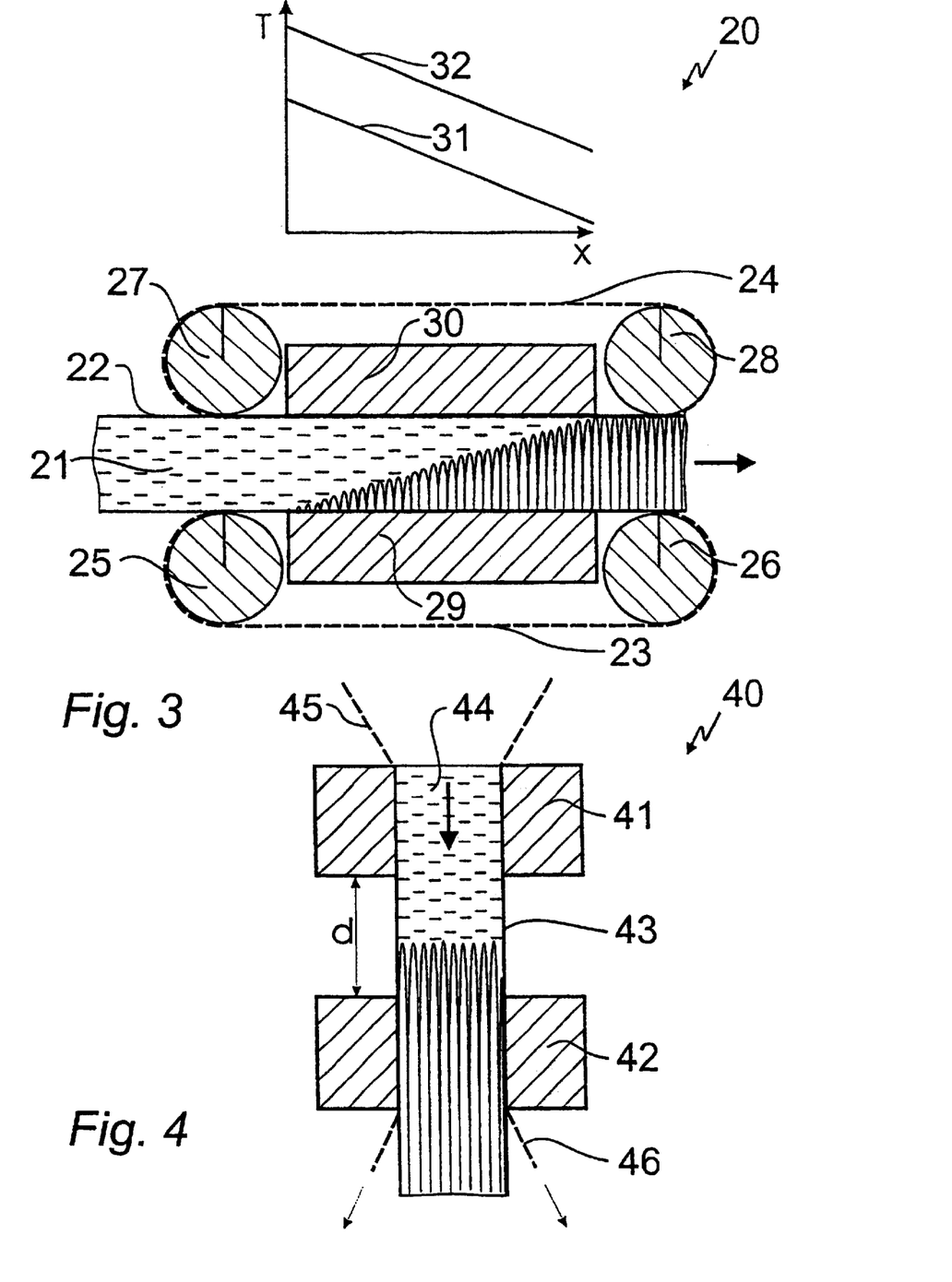
FIG. 3. A device for producing porous structures in the continuous process with a schematic rendering of the temperature control shown above.
FIG. 4. A further device for producing porous structures in the continuous process.

FIG. 3 illustrates a continuous device 20. The function of the specimen space 21 is carried out in this case by a hose 22 that leads between two conveyor belts 23, 24. The conveyor belts 23 and 24 are each driven by a pair of drive rollers 25, 26 and 27, 28 respectively. Between these rollers, a cooling element 29 and 30 respectively is arrayed on the upper side and on the lower side of the hose 22. These cooling elements 29 and 30 are constructed in such a way that they generate a temperature gradient along their length that affects the specimen space 21. For this purpose, the cooling elements 29, 30 can be constructed in segments, in order to generate a temperature reduction by stages. Nevertheless, it is advantageous to have a practically continuous temperature reduction, as in the case of the one illustrated in the graph above the device. This graph plots the temperature along the length of the cooling elements 29, 30. The straight line 31 represents the temperature gradient on the lower side of the specimen space 21, while the straight line 32 represents the temperature gradient on the upper side of the specimen space 21. This graph shows that the difference between the temperatures at opposing points between the cooling elements 29, 30 is kept constant when the cooling rate is constant.

When this device 20 is used, a liquid or pasty mixture is introduced into the hose 22 in the specimen space 21 on the left-hand side. The said hose is fed through between the cooling elements 29 and 30 at an unchanging speed by means of the conveyor belts 23 and 24, so that an ice front advances from the lower side to the upper side of the hose 22 as a result of the cooling within the said hose, which should have advanced right through the entire specimen by the end of the cooling elements 29 and 30, so that the frozen specimen can subsequently be freeze-dried in a vacuum chamber (not illustrated).

The hose 22 may have a rounded, squared or other form of cross section, so that, as a function of the case of application, the device can be used in the continuous process to generate especially shaped components, such as rods or plates.

The device 20 can also be equipped with lateral delimitations, so that the specimen can be conducted between the cooling elements without using a hose. In addition, the specimen can also be conducted between two individual membranes.

A further continuous device is illustrated in FIG. 4. In this device, the liquid is conducted into a tube 43 between two cooling elements 41, 42 arrayed at a distance from each other. The distance d between the cooling elements 41 and 42 creates a space between the cooling elements in which a temperature gradient can be adjusted. When a liquid or a pasty medium 44 is introduced into the hopper-shaped upper side 45 of the tube 43, the specimen passes into the space between the cooling elements 41 and 42, so that an ice front is formed between the said cooling elements when it flows through the said tube 43. The consequence of this is that the frozen specimen leaves the device 40 at the hopper-shaped lower side 46 of the said device in order to pass on to subsequent freeze-drying.

In a manner comparable to that described above in the case of the device 20, the specimen may also be conducted in a hose or between membranes in the case of a lateral array for the device 40.

It is possible to array a membrane heating element between the cooling elements 29 and 31 or 41 and 42 and the specimen for the purpose of achieving a simpler and more accurate adjustment of the temperature controls also in the case of the continuous devices.

Figure 5:
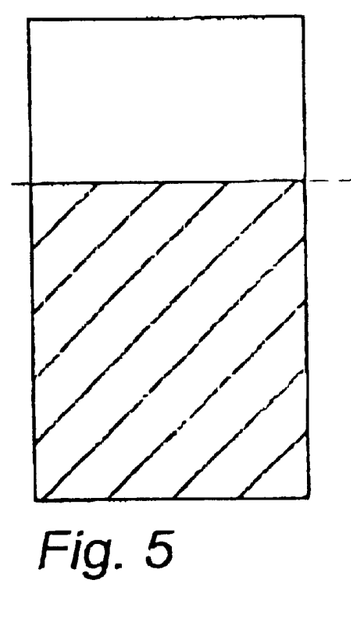
FIG. 5. A homogeneously uniform structure of an aqueous collagen suspension.
Figure 6:
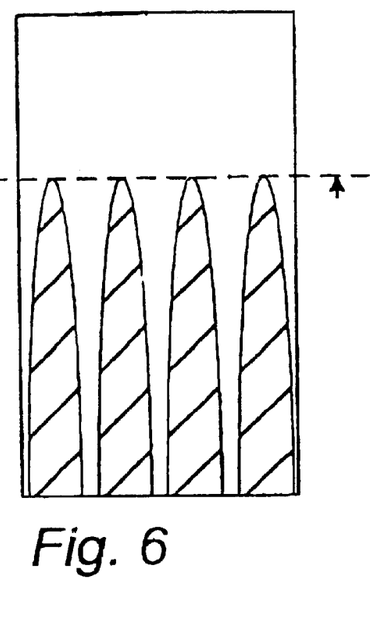
FIG. 6. A homogeneously finger-shaped ice crystal structure of an aqueous collagen suspension, and FIG. 7. A representation of the pore size in relation to the concentration of acetic acid.

FIGS. 5 and 6 illustrate two typical variants on the cooling according to the invention of possible homogeneous structures, using the example of a schematically illustrated aqueous collagen suspension. The cooler side is situated in the lower area of the figures, the warmer side in the upper area. The direction in which the solidification front advances is thus from bottom to top.

Before the solidification starts, the collagen fibers are distributed relatively evenly. If no additives are added to the approximately two percent by weight collagen suspension, a process temperature control leads to a smooth advance of the ice front, as described in FIG. 2, wherein the position and distribution of the fibers, as illustrated in FIG. 5, remain substantially unaltered. The area that has already crystallized is represented by cross-hatching in the figures.

If additives that lower the freezing point, such as acetic acid or ethanol, are added to the collagen suspension and the solidification parameters are selected correctly, the result is the formation of the finger-shaped ice crystal structures shown in FIG. 6, which are once again represented by cross-hatching. This involves the collagen fibers in a change of their orientation, in addition to which they mesh together in the channels between the ice fingers. During freeze-drying, the ice is removed by sublimation and the desired porous structures remain.

The morphology of the ice crystals and thus the size of the pores can be pre-determined by selecting the type and concentration of the additive, the concentration of the collagen, the temperature gradient over the mixture and the rate of cooling of both specimen delimitations.

Figure 7:
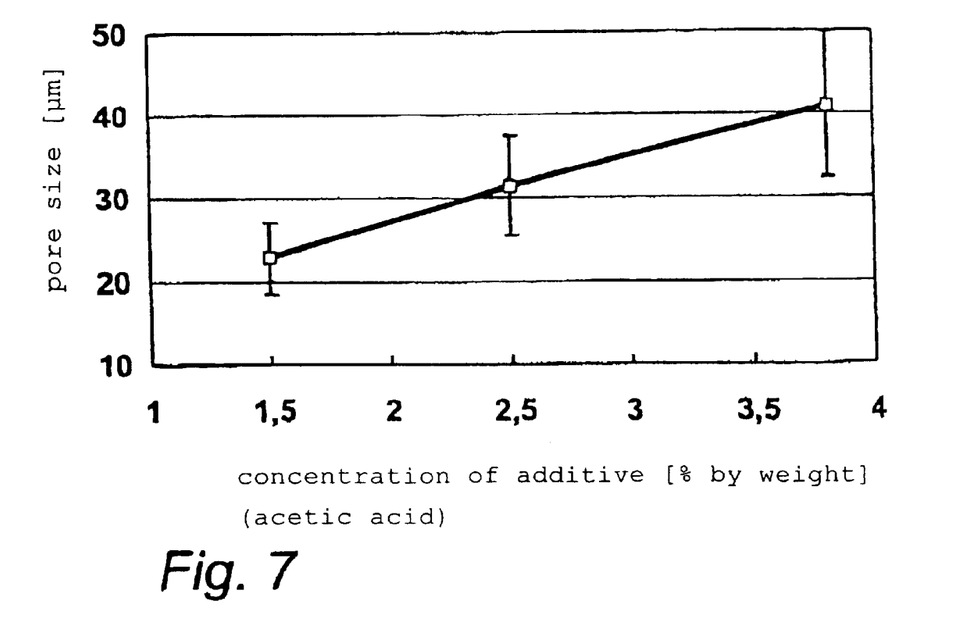

FIG. 7 uses the example of a 1.8 percent by weight collagen suspension frozen at a rate of cooling of 9 K/min and with a temperature gradient of 50 K/cm to illustrate the influence exerted by an additive of acetic acid on the size of the pores. (The shortest measurement through the non-circular pores is always given as the pore size.) The concentration of the additive in percentage of weight (acetic acid) is plotted on the abscissa and the pore size in $\mu$ on the ordinate.

Optimal parameter ranges:

| | |
|---|---|
| Temperature gradient generated: | 1 K/cm to 100 K/cm |
| Advantageous: | 10 K/cm to 60 K/cm |
| Additive concentration: | 0.1 to 25 percent weight |
| advantageous: | 1 to 10 percent weight |
| Rate of cooling: | 0.1 K/min to 500 K/min |
| advantageous: | 1 K/min to 50 K/min |

6. EXAMPLES

The following are two specific examples illustrating different methods of carrying out the invention. The experiments in these examples were carried out with a collagen dispersion that was prepared according to German Patent Application No. DE 40 28 622 A 1. This collagen dispersion contains 1.8 wt % collagen in water and HCl to adjust the pH value to approximately 3.2. The collagen preparation is a fibrillar, insoluble type 1 collagen that is isolated from bovine skin. The dispersion is a polydisperse system containing low concentrations of collagen molecules, fibrills, and fibers.

The inventors have shown that the desired homogeneous porous structures can be achieved with other collagen dispersions from other manufactures as well, that were prepared according to different methods. However, the optimization of the influencing parameters is specific for every collagen dispersion and may result in slightly different process parameters.

6.1 Example 1

Production of a Collagen Sponge with Homogeneously Distributed Collagen Fibers with Random Orientation In this example, a collagen sponge without a redistribution of the collagen fibers during the freezing process (c.f. FIG. 5) is produced by the following method:

The basic collagen suspension (5) is inserted between the upper (13) and lower (12) temperature controlled surface of FIG. 1. The thickness of the collagen dispersion is 10 mm, the surface area is currently 83 mm×83 mm. The sample is laterally surrounded by a PTFE frame (4). The initial surface temperatures (warmer surface 37° C., colder surface approximately 0° C.) are shown in FIG. 2. After an initial temperature equilibration, the colder surface was cooled at a rate of −9° C./min.

After a temperature gradient of 50° C./cm between the lower and upper surface was established, both surfaces were cooled at the same cooling rate of −9° C./min until the lower surface temperature reached approximately −75° C. This low temperature was chosen in order to provide a safety margin. In principle, the solidification procedure can be stopped earlier. Then the upper surface is removed pneumatically and the frozen collagen dispersion is transferred to a mechanical freezer for at least 24 h at −80° C. Elevated temperatures (below 0° C.) can also be used, however the effect on further cross-linking or redistribution should be considered when using such temperatures.

Finally, the solidified samples were vacuum-dried in a freeze-dryer. To avoid a partial melting of the samples the shelf was pre-cooled with liquid nitrogen. No temperature control was used during the drying phase in these initial experiments. The chamber pressure was set to 0.04 mbar and the condenser temperature was approximately −55° C.

In order to increase the degree of cross-linking, the sponges can also be further modified under a vacuum atmosphere at elevated temperatures, preferably no higher than about 160° C.

In collagen sponges that are produced according to this method the collagen fibers are distributed homogeneously as shown schematically in FIG. 5. However, open porous structures are not achieved. This is due the fact that a planar ice front grows across the entire sample under these freezing conditions. As can be observed in microscopic studies the collagen fibers are directly encapsulated in the ice front without a significant redistribution and thus exhibit a random orientation.

6.2 Example 2

Production of a Collagen Sponge with a Homogeneous Pore Size and Structure

Preparation of collagen sponges with a porous structure according to the sketch in FIG. 6 is enhanced by providing a significant constitutional supercooling ahead of the ice front. For this purpose suitable solutes may be added. In this example we added 3.8 wt % acetic acid to the basic collagen dispersion mentioned in Example 1. The dispersion was then centrifuged for 10 min at 225 g to remove air bubbles. The further processing of the collagen dispersion was identical to Example 1. However, due to the additional component and the chosen freezing parameters a cellular crystallization structure as shown in FIG. 6 was achieved, and the collagen fibers were not incorporated into the growing ice crystals but were rejected. The fibers were highly concentrated within the channels between the ice crystals.

During freeze-drying, which was also performed as in Example 1, the water was removed and open porous structures remain. The resulting pore size was about 40 mm. The pores were open from the bottom to the top of the sponge and were very homogeneous in structure and size. This homogeneity is a major advantage over currently available sponges. FIG. 7 shows further pore sizes that can be achieved for other acetic acid concentrations when appropriate freezing parameters are chosen.

It should be mentioned that the foregoing description should be only considered to be illustrative and not restrictive.

What is claimed is:

1. A method for producing porous structures, the method comprising:
   (a) providing an at least partially solidified product by bringing a liquid or pasty mixture of substances at least partially to solidification between two surfaces with different temperatures that can be tempered and are set at a distance from each other that results in the generation of a substantially ordered structure;
   (b) freeze-drying the at least partially solidified product of (a).

2. The method of claim 1, wherein the difference between the temperatures of the opposing surfaces is kept substantially constant during the cooling step.

3. The method of claim 1, wherein the temperature of one surface area is kept constant until the other surface area has cooled sufficiently to create a temperature gradient that results in the generation of a substantially ordered structure.

4. The method of claim 1, wherein the surfaces are arrayed parallel to each other.

5. The method of claim 1, wherein the surfaces are arrayed concentrically.

6. The method of claim 1, wherein the mixture is introduced on a first side between the surfaces and on a second side let out between surfaces, while the temperature of the opposing surface areas drops from the first side to the second side.

7. The method of claim 1, wherein the mixture is fed through or along heat conducting conveyor belts or hoses.

8. The method of claim 1, wherein the at least partially solidified product is freeze-dried, as one surface is removed and the other surface is tempered.

9. The method according to claim 1, wherein an aqueous solution or suspension is used as the liquid or pasty mixture.

10. The method according to claim 1, wherein an active ingredient or additive is added to the liquid or pasty mixture.

11. The method according to claim 1, wherein biologically active materials, living cells and/or cryoprotection are added to the liquid or pasty mixture.

12. The method according to claim 1, wherein an active ingredient or an additive of biologically active materials or living cells is added to the freeze-dried structure.

13. The method of claim 1, wherein additional gases are dissolved in the mixture.

14. The method of claim 1, wherein, after cooling has been completed, the mixture is warmed back up to a re-crystallization temperature and kept there for a given amount of time before being freeze-dried.

15. The method of claim 1, wherein foreign materials in preferred geometries and orientations are introduced into the liquid or pasty mixture and only removed after the freeze-drying.

16. The method of claim 1 wherein the porous structure is a medicinal or pharmaceutical product or product of environmental and bio-technology.

17. The method of claim 1 wherein the porous structure is a cosmetic or medicinal product.

18. The method of claim 1 wherein the liquid or pasty mixture is a collagen suspension.

19. A method for producing porous structures, comprising the steps of:
   (a) providing a liquid or pasty mixture of substances;
   (b) cooling the mixture under pressure until shortly before the solidification point of such mixture;
   (c) subjecting the mixture to sudden depressurization, wherein the sudden depressurization causes crystallization of the cooled mixture and simultaneous formation of homogeneously distributed ice crystals throughout the mixture; and (d) subsequently freeze-drying the mixture to form homogeneously porous structures.

20. A method for producing porous structures in which a liquid or pasty mixture of substances is brought at least partially to solidification and subsequently freeze-dried, wherein the mixture is pre-cooled under pressure and subsequently suddenly depressurized, and wherein the pressure is in the range from 1 to 250 MPa.

* * * * *

UNITED STATES PATENT AND TRADEMARK OFFICE
CERTIFICATE OF CORRECTION

PATENT NO.    : 6,447,701 B1
DATED         : September 10, 2002
INVENTOR(S)   : Günter Rau and Ingo Heschel It is certified that error appears in the above-identified patent and that said Letters Patent is hereby corrected as shown below:

Column 1,
Line 48, "freeze-dried The" should be -- freeze-dried. The --

Column 8,
Line 21, "in $\mu$ on" should be -- in $\mu$m on --

Signed and Sealed this

Seventh Day of October, 2003

JAMES E. ROGAN
*Director of the United States Patent and Trademark Office*